(12) United States Patent
Croteau

(10) Patent No.: US 12,121,263 B2
(45) Date of Patent: Oct. 22, 2024

(54) FOOT OPERATED TRACTION DEVICE AND METHOD OF USING SAME FOR MECHANICAL CERVICAL RIPENING

(71) Applicant: VALDI MEDICAL INC., Gatineau (CA)

(72) Inventor: Diane Croteau, Gatineau (CA)

(73) Assignee: VALDI MEDICAL INC., Gatineau (CA)

( * ) Notice: Subject to any disclaimer, the term of this patent is extended or adjusted under 35 U.S.C. 154(b) by 0 days.

(21) Appl. No.: 18/394,844

(22) Filed: Dec. 22, 2023

(65) Prior Publication Data

US 2024/0122621 A1   Apr. 18, 2024

Related U.S. Application Data

(62) Division of application No. 17/250,274, filed as application No. PCT/CA2019/050905 on Jun. 28, 2019, now Pat. No. 11,903,614.

(30) Foreign Application Priority Data

Jul. 5, 2018 (GB) ...................................... 1811085

(51) Int. Cl.
*A61M 29/02* (2006.01)
*A61B 17/42* (2006.01)

(52) U.S. Cl.
CPC ............. *A61B 17/42* (2013.01); *A61M 29/02* (2013.01); *A61B 2017/4225* (2013.01); *A61M 2205/586* (2013.01); *A61M 2210/1433* (2013.01)

(58) Field of Classification Search
CPC ............ A61B 17/42; A61B 2017/4225; A61B 2017/00557; A61B 2017/00973; A61B 17/12136; A61B 2017/4216; A61B 17/0218; A61B 17/0057; A61B 17/00234; A61B 17/12099; A61B 2017/22062;
(Continued)

(56) References Cited

U.S. PATENT DOCUMENTS 4,150,676 A * 4/1979 Jackson ................ A61M 16/04
128/207.18
4,589,410 A * 5/1986 Miller ................... A61M 16/04
D24/129

(Continued)

*Primary Examiner* — Mohamed G Gabr
*Assistant Examiner* — Aman Kumar Mann
(74) *Attorney, Agent, or Firm* — LAVERY, DE BILLY, LLP; Gonzalo Lavin

(57) ABSTRACT

A foot operated traction device for allowing a pregnant woman to selectively self-induce dilatation of her cervix via her foot and a method for doing the same, the device comprising a balloon catheter comprising an inflatable balloon insertable above the cervix of the pregnant woman and an elongate catheter tube comprising a catheter tube proximal end portion and a catheter tube distal end portion coaxially mounted to the inflatable balloon, the inflatable balloon inflatable with a fluid to apply dilatative pressure against the cervix, and an elongate stirrup connected to the catheter tube at the catheter tube proximal end at a stirrup proximal end and removably engageable with the foot of the pregnant woman at a stirrup distal end, wherein the stirrup distal end is movable by the movement of the foot to selectively vary a traction force of the inflatable balloon.

15 Claims, 6 Drawing Sheets

(58) Field of Classification Search
CPC .......... A61B 17/0281; A61B 17/12022; A61B 17/1204; A61B 17/1219; A61M 29/02; A61M 2205/586; A61M 2210/1433; A61M 25/1011; A61M 25/1002; A61M 16/0409; A61M 16/04; A61M 25/10; A61M 2210/1475; A61M 2210/14
See application file for complete search history.

(56) References Cited

U.S. PATENT DOCUMENTS

| | | | |
|---|---|---|---|
| 2008/0215031 A1* | 9/2008 | Belfort | A61B 17/12099 606/192 |
| 2015/0045809 A1* | 2/2015 | Nowak | A61B 17/42 606/119 |

* cited by examiner

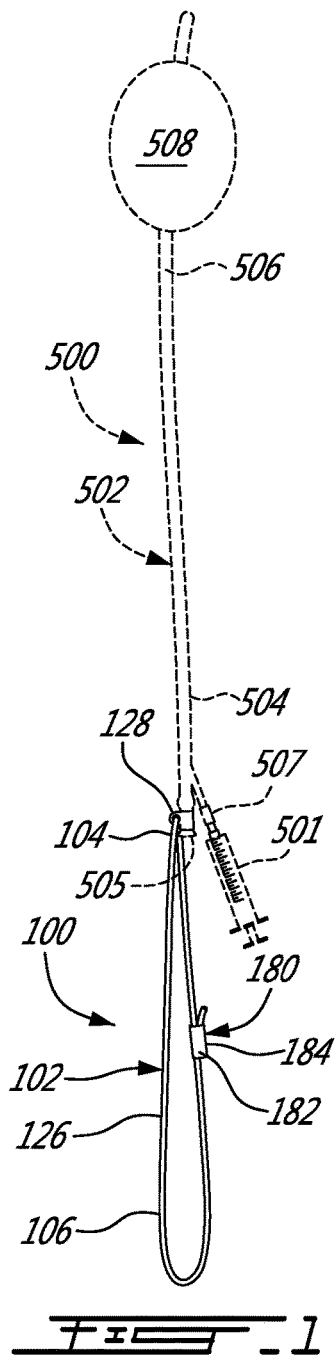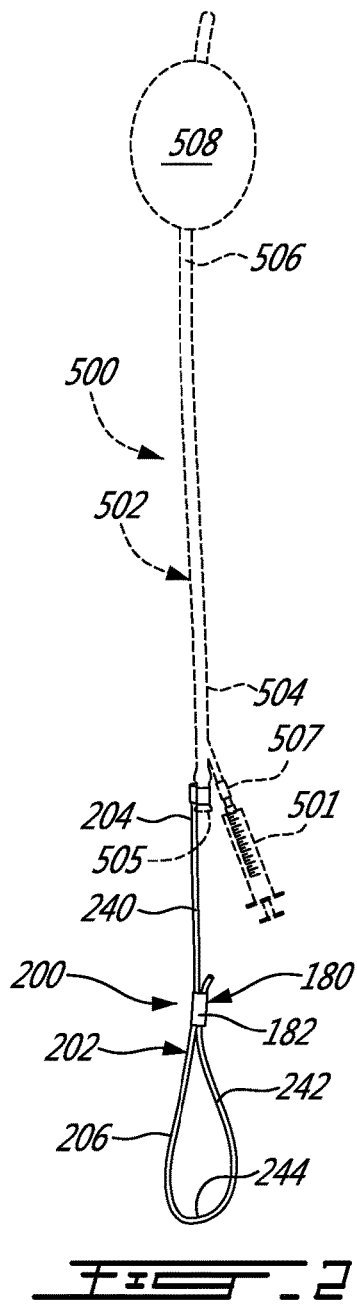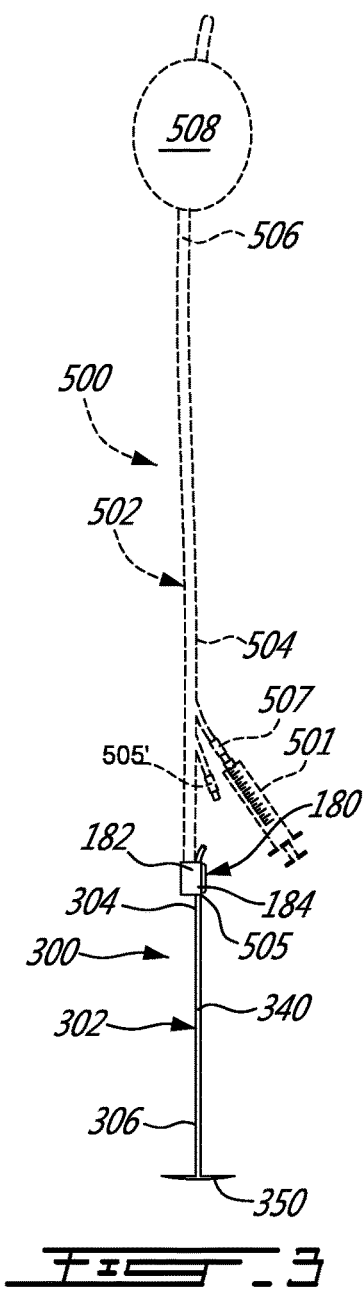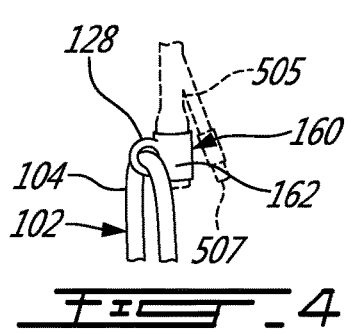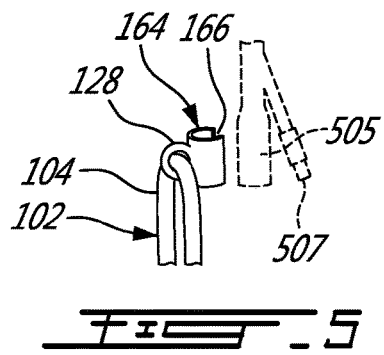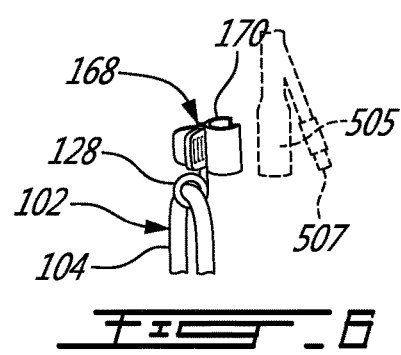

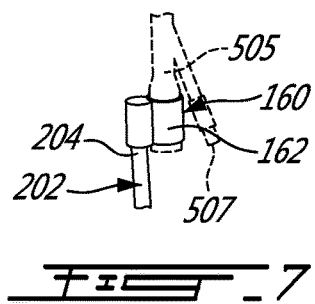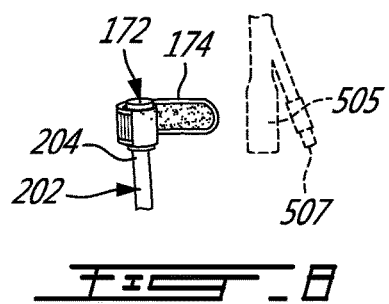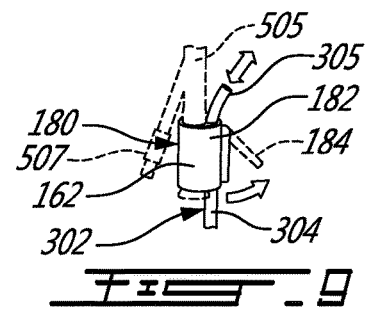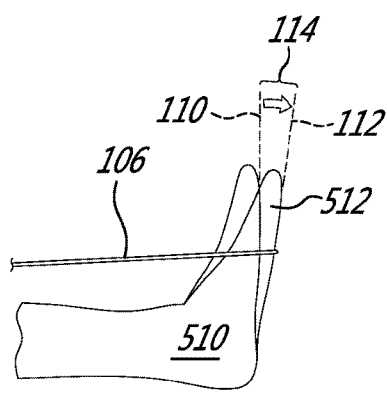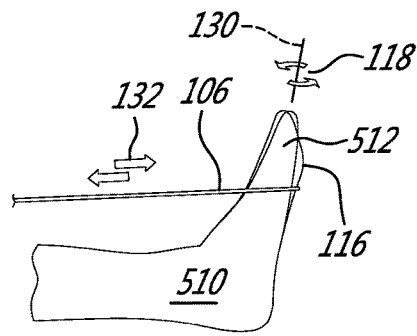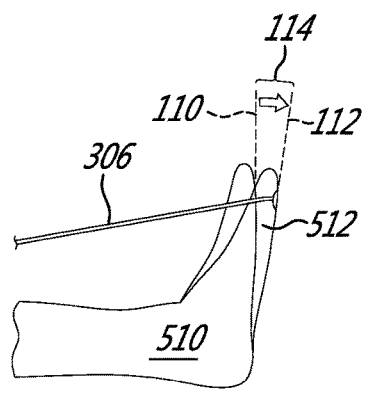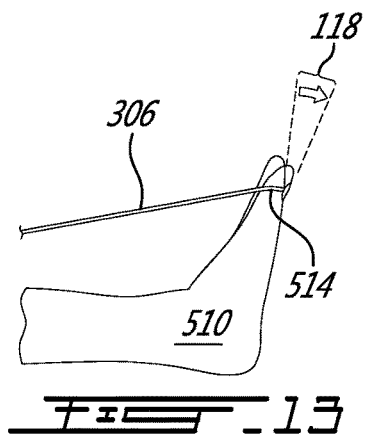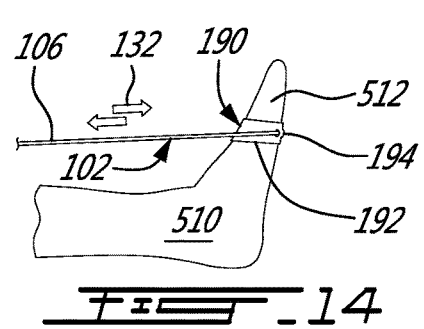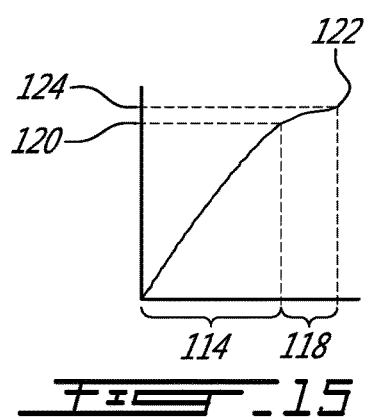

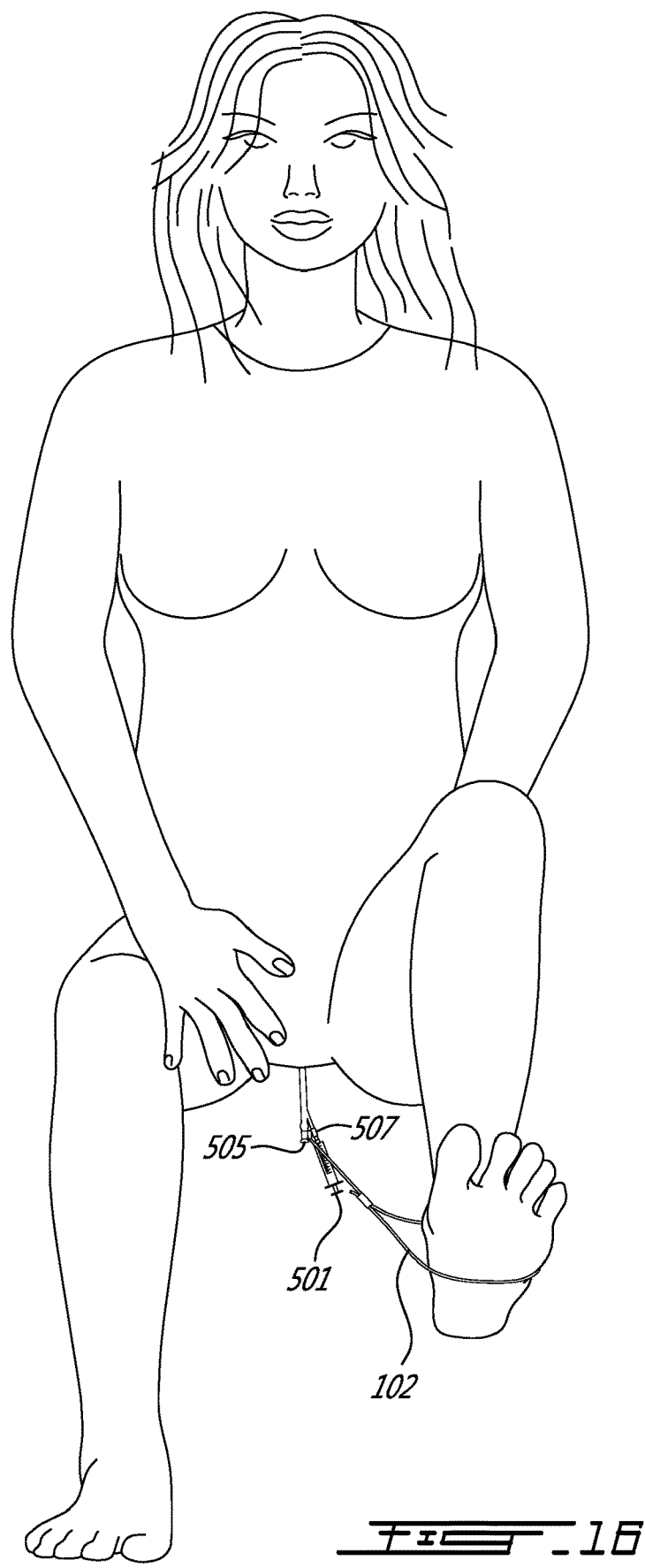

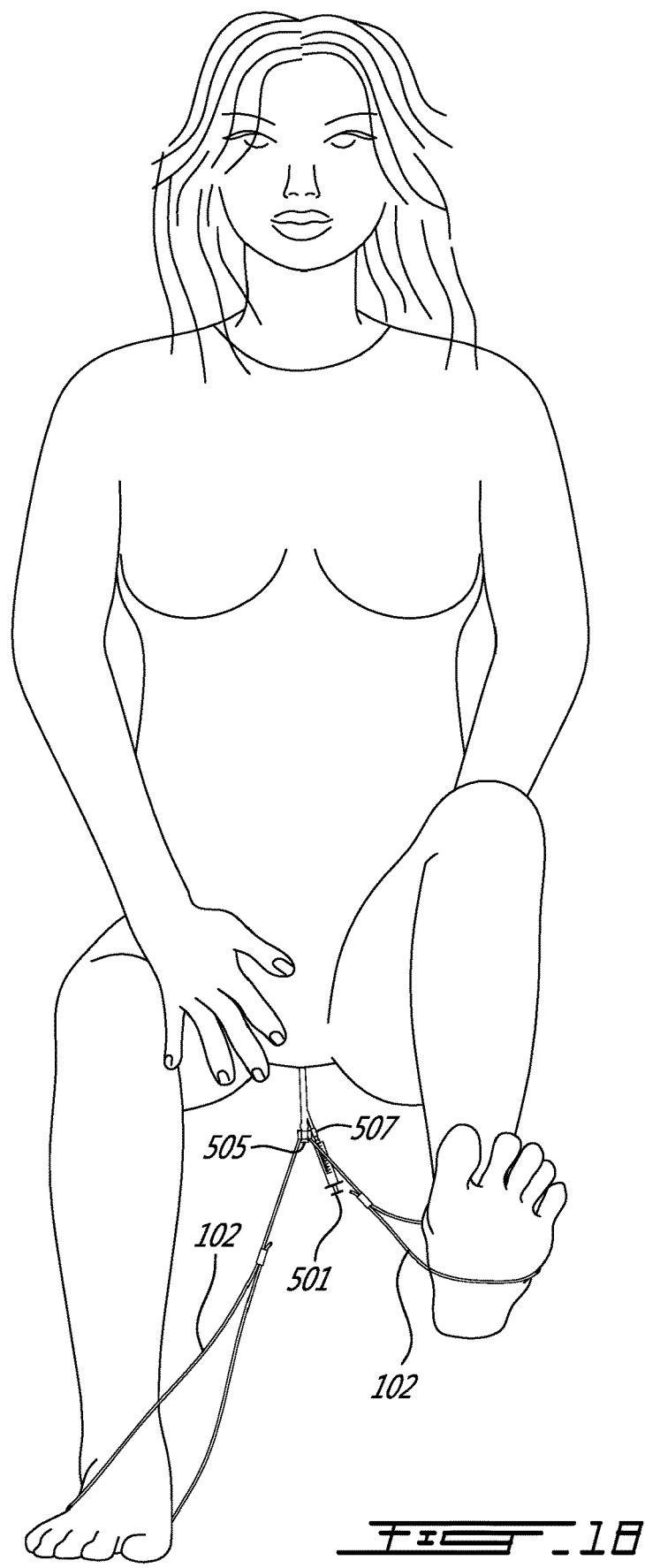

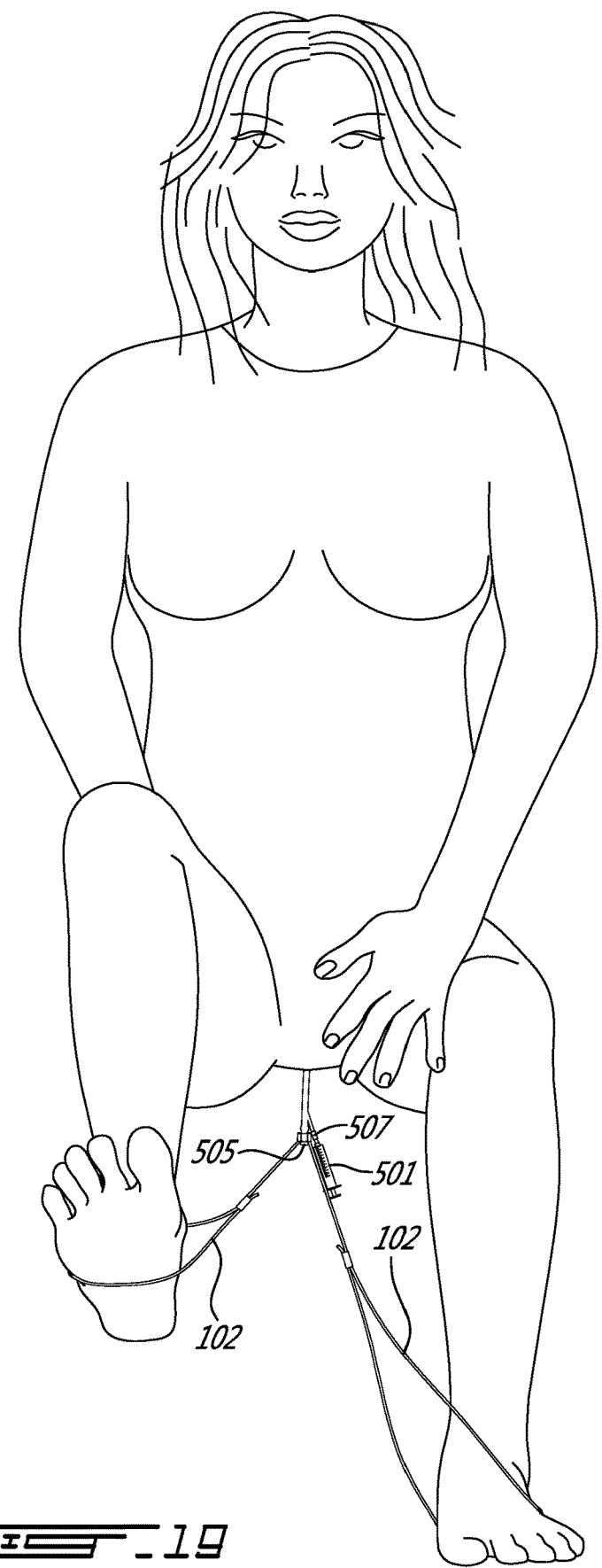

FOOT OPERATED TRACTION DEVICE AND METHOD OF USING SAME FOR MECHANICAL CERVICAL RIPENING

CROSS-REFERENCE TO RELATED APPLICATIONS

This application is a divisional application of U.S. patent application Ser. No. 17/250,274 filed on Dec. 23, 2020, which was a National Entry Application of PCT application No. PCT/CA2019/050905 filed on Jun. 28, 2019 and published in English under PCT Article 21(2), which itself claims benefit of Great Britain patent application Serial No. 1811085.8, filed on Jul. 5, 2018. All documents above are incorporated herein in their entirety by reference.

FIELD OF THE INVENTION

The present invention relates generally to traction devices and, more specifically, to a foot operated traction device for rapid cervical dilatation particularly adapted for allowing a pregnant woman to selectively self-apply a controlled traction force on a balloon catheter inserted above her cervix for artificially inducing a proper dilatation thereof, and a method of performing the same for mechanical cervical ripening.

BACKGROUND OF THE INVENTION

In the last phases of pregnancy, for pregnant women requiring an induction of labour and having a relatively low Bishop score, it is often recommended to use a balloon catheter, such as a Foley or the Cook cervical ripening balloon or equivalent, for artificially promoting the dilatation of their cervix. In addition, cesarean section rates in Canada are estimated between 20-25%, it is contraindicated to use prostaglandins for cervical ripening in a woman having had a previous cesarean. Mechanical dilatation with medical grade balloons may be used in these women. The Cook device, which normally uses two balloons, is not optimal at creating adequate dilatation and effacement, and, is a relatively expensive product.

Briefly described, the conventional method of use of the balloon catheter typically involves inserting the balloon element of the catheter above the cervix of the pregnant woman, followed with inflating the balloon with a sterile solution, then maintaining a predefined level of traction force on the elongated outer end portion of the balloon catheter by securing this outer end portion to one of the pregnant woman's legs using, typically, a medical grade adhesive tape.

While this conventional method can generally fulfill the general objective of maintaining a traction force on the balloon catheter, it also generally implies one or more of the following disadvantages.

For example, after a balloon catheter has been properly installed and a suitable level of traction force has been applied for a given period of time, the dilatation of the pregnant woman's cervix will have progressed to a point where the level of traction force on the balloon catheter is no longer effective. Hence, medical personnel must regularly dedicate time at various intervals to readjust the traction force on the catheter balloon to a suitable level. This results in less precise results as the medical personnel, such as nurses, must adjust the pulling or traction force in a non-optimal manner. In addition, the traction may be quite uncomfortable or even painful for the pregnant woman and is not an ergonomic position for the patient, the adhesive tapes to secure the elongated portion also frequently loses its adhesive properties thus decreasing the traction.

Furthermore, as is well known in medical facilities, time is often a luxury and such regular interventions by medical personnel to readjust the level of traction force on the catheter balloon may be delayed, sometimes repeatedly. It may also delay the time to labour and delivery. Consequently, the pregnant woman must spend more time in the medical facility as she waits for her cervix to sufficiently dilate, along with all the incurred costs. As the foot operated traction device involves participation by the pregnant woman, she is more rapidly aware of the loss of tension which indicates that sufficient dilatation is obtained.

Thus, there is a need for an improved device and method for artificially promoting the dilatation of the cervix of a pregnant woman that avoids the aforementioned disadvantages.

SUMMARY OF THE INVENTION

In a broad aspect, the present invention provides a foot operated traction device for allowing a pregnant woman to selectively self-apply a controlled traction force level on a balloon catheter having an inflatable balloon inserted above her cervix for inducing dilatation thereof, and a method of performing the same.

According to an embodiment of the present invention, there is a provided foot operated traction device for allowing a pregnant woman to selectively self-induce dilatation of her cervix via her foot. The device components are: a balloon catheter comprising an inflatable balloon insertable above the cervix of the pregnant woman and an elongated elastic catheter tube comprising a catheter tube with proximal and distal end portions coaxially mounted to the inflatable balloon. The inflatable balloon inflatable with a sterile fluid to apply dilatative pressure against the cervix, and an elongated stirrup connected to the proximal end of the catheter at a stirrup proximal end and removably engageable with the foot of the pregnant woman at a stirrup distal end, wherein the stirrup distal end is movable by the movement of the foot to selectively vary a traction force of the inflatable balloon upon the cervix.

In an embodiment, the stirrup distal end is engageable with the foot of the pregnant woman at a foot forward end portion.

In an embodiment, the stirrup distal end is movable between a stirrup distal end first position and a stirrup distal end second position, the stirrup distal end second position positioned further away from the cervix than the stirrup distal end first position, through a first movement of the foot forward end portion.

In an embodiment, the stirrup distal end is further movable between the stirrup distal end second position and a stirrup distal end third position, the stirrup distal end third position positioned further away from the cervix than the stirrup distal end second position, through a second movement of the foot forward end portion.

In an embodiment, the first movement comprises a forward pivotal movement of the foot forward end portion.

In an embodiment, the second movement comprises at least one of an inward twisting movement of the foot forward end portion about a longitudinal axis thereof and a forward bending of the toes of the foot.

In an embodiment, the second movement increases the traction force at a lower rate than the first movement.

In an embodiment, the elongate stirrup comprises a closed loop element slideably engageable with an eyelet structure connecting the elongate stirrup to the catheter tube proximal end portion.

In an embodiment, the elongate stirrup comprises an elongated stirrup extension segment connected at one end thereof to the catheter tube proximal end portion and at another end thereof to a stirrup end loop segment.

In an embodiment, the elongate stirrup comprises an elongated stirrup extension segment connected at one end thereof to the catheter tube proximal end portion and at another end thereof to a transversal toe engaging member comprising a substantially T-shaped configuration and engageable and retainable between two toes of the foot.

In an embodiment, the stirrup proximal end is connected to the catheter tube proximal end portion via one of a connector comprising a tubular portion fixedly and coaxially mounted to the catheter tube proximal end portion, a connector comprising a connector longitudinal slot comprising a C-shaped cross section removably and transversally engageable with the catheter tube proximal end portion, or a connector comprising a spring-biased manual clamp element removably and transversally engageable with the catheter tube proximal end portion.

In an embodiment, the stirrup proximal end is connected to the catheter tube proximal end portion via one of a connector comprising a tubular portion fixedly and coaxially mounted to the catheter tube proximal end portion or a connector comprising a hook-and-loop fastener removably and transversally engageable with the catheter tube proximal end portion.

In an embodiment, the device further comprises an adjustable element connected to the stirrup element between the stirrup proximal end and the stirrup distal end, the adjustable element configured to adjust the length of the stirrup element.

In an embodiment, the device further comprises a removable stirrup holder comprising a foot band comprising a stirrup guide, the removable stirrup holder configured for maintaining a distal portion of the stirrup element substantially in position across the underside of the foot forward end portion.

The present disclosure also provides a method for selectively self-inducing the dilatation of a pregnant woman's cervix via her foot, comprising the steps of inserting an inflatable balloon of a balloon catheter above the cervix, the balloon catheter connected to an elongate stirrup at a stirrup proximal end, inflating the inflatable balloon with a fluid, removably engaging a stirrup distal end of the elongate stirrup to a foot forward end portion of the foot of the pregnant woman, and performing a movement of the foot to apply a traction force on the inflated inflatable balloon, the traction force applying a dilatative pressure against the cervix.

In an embodiment, the performing a movement of the foot comprises a first movement of the foot forward end portion wherein the stirrup distal end is moved between a stirrup distal end first position and a stirrup distal end second position, the stirrup distal end second position positioned further away from the cervix than the stirrup distal end first position.

In an embodiment, the performing a movement of the foot further comprises a second movement of the foot forward end portion wherein the stirrup distal end is further moved between the stirrup distal end second position and a stirrup distal end third position, the stirrup distal end third position positioned further away from the cervix than the stirrup distal end second position.

In an embodiment, the second movement increases the traction force at a lower rate than the first movement.

Other advantages, novel features and alternate embodiments of the present invention will be more apparent from the following drawings and detailed description.

BRIEF DESCRIPTION OF THE DRAWINGS

FIG. 1 is a perspective view of a traction device, according to an embodiment of the present invention;

FIG. 2 is in a perspective view of a traction device, according to another embodiment of the present invention;

FIG. 3 is a perspective view of a traction device, according to yet another embodiment of the present invention;

FIG. 4 is a perspective view of an embodiment of a connector for the traction device of one of FIG. 1, 2 or 3;

FIG. 5 is a perspective view of another embodiment of a connector for the traction device of one of FIG. 1, 2 or 3;

FIG. 6 is a perspective view of yet another embodiment of a connector for the traction device of one of FIG. 1, 2 or 3;

FIG. 7 is a perspective view of yet another embodiment of a connector for the traction device of one of FIG. 1, 2 or 3;

FIG. 8 is a perspective view of yet another embodiment of a connector for the traction device of one of FIG. 1, 2 or 3;

FIG. 9 is a perspective view of yet another embodiment of a connector, here shown combined with an adjustment element, for the traction device of one of FIG. 1, 2 or 3;

FIG. 10 is a side elevation view of the traction device of one of FIG. 1 or 2, here shown having a foot engaged in a portion thereof and achieving a first movement;

FIG. 11 is a side elevation view of the traction device of one of FIG. 1 or 2, here shown having a foot engaged in a portion thereof and achieving a second movement;

FIG. 12 is a side elevation view of the traction device of FIG. 3, here shown having a foot engaged in a portion thereof and achieving a first movement;

FIG. 13 is a side elevation view of the traction device of FIG. 2, here shown having a foot engaged in a portion thereof and achieving a second movement;

FIG. 14 is in a graphical view of the progressions of various levels of traction force applied to the traction device of one of FIG. 1, 2 or 3;

FIG. 15 is in a side elevational view of a stirrup element holder engaged on a foot forward end portion for the traction device of one of FIG. 1 or 2;

FIGS. 16 and 17 are top views of a traction device being used by a pregnant woman with a single foot, according to an embodiment of the present invention FIGS. 18 and 19 are top views of a traction device being used by a pregnant woman with her two feet, according to an embodiment of the present invention.

DESCRIPTION OF ILLUSTRATIVE EMBODIMENTS

Figure 17:
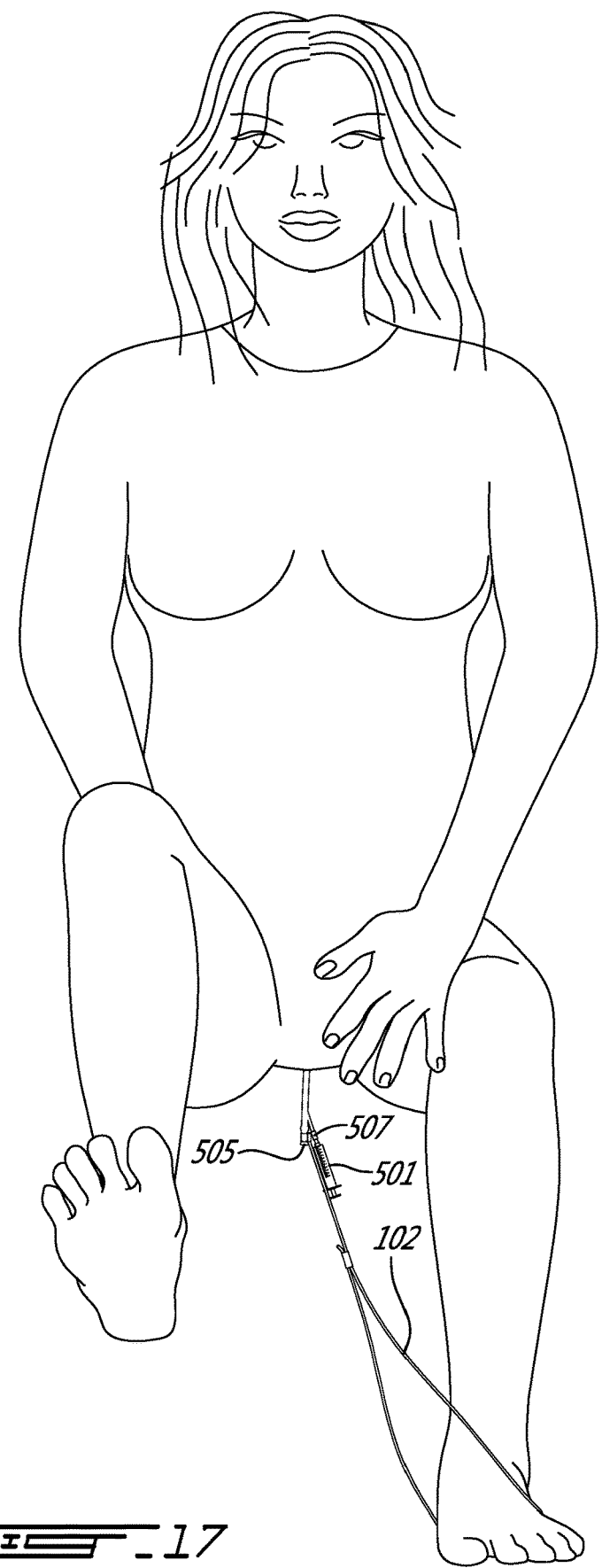

FIG. 1 illustrates various aspects of an embodiment of a foot operated traction device 100 according to the present invention, hereinafter referenced more simply as traction device 100. Traction device 100 allows a pregnant woman to selectively self-apply a controlled traction force level on a balloon catheter 500 having an inflatable balloon 508 inserted inside her cervix for artificially inducing dilatation thereof. Typically, the balloon catheter 500 includes an elongated catheter tube 502. The catheter tube 502 includes a catheter tube proximal end portion 504 and a catheter tube distal end portion 506, to which is coaxially mounted the inflatable balloon 508. The traction device 100 further includes a stirrup element 102 having a substantially elongated configuration. The stirrup element 102 defines a stirrup proximal end 104 connected along the catheter tube proximal end portion 504, and a stirrup distal end portion 106 configured for removably engaging the foot forward end portion 512 of a foot 510 of the pregnant woman, as illustrated, for example, in FIG. 10.

The balloon catheter 500 with inflatable balloon 508 may be of a known type, such as those used for insertion in the urethra of a patient. A syringe 501 (also shown in FIGS. 16 to 19) is used to fill the balloon 508 with fluid or air via a first bottom tube 507 near the end portion 504 that extends from the catheter tube 502. The first bottom tube defines an inner channel in the catheter tube 502 for filling the balloon 508 located near the distal end portion 506. A second larger tube 505 near the end portion 504 is typically used for connecting to a urine bag. However, as described further below, the second larger tube is used to receive connector 160 for holding stirrup 106. In the version shown in FIG. 3, the catheter tube 502 has near its end portion 504 two larger tubes 505, 505' that are normally used for connecting to respective urine bags. Other pumping means than the syringe 501 may be used for filling the balloon 508 as persons skilled in the art will understand.

Still referring to FIG. 1 in addition to, for example, FIG. 10, in an embodiment the stirrup distal end portion 106 is movable between a stirrup distal end first position 110 and a stirrup distal end second position 112 through a first movement 114 of the forward end portion of the foot 512, wherein the stirrup distal end second position 112 is further away from the cervix of the pregnant woman than the stirrup distal end first position 110. The stirrup distal end portion 106 is further movable between the stirrup distal end second position 112, as illustrated in FIG. 10, and a stirrup distal end third position 116, as illustrated in FIG. 11, through a second movement 118 of the forward end portion of the foot 512, wherein the stirrup distal end third position 116 is further away from the cervix of the pregnant woman than the stirrup distal end second position 112. Furthermore, the first movement 114 achieved with the foot forward end portion 512 is different from the second movement 118. In addition, the stirrup distal end portion 106 is configured to take advantage of the shape configuration of the foot forward end portion 512 as it performs the second movement 118. As such, the pregnant woman may selectively apply a relatively more controlled and, thus, more precise level of traction force on the balloon catheter 500 by using the second movement 118 compared to when using the first movement 114 of the foot 510.

Referring to FIG. 14, a preferred method of use of the traction device 100 will now be described. In a first step, the inflatable balloon 508 is inserted above the pregnant woman's cervix, preferably by medical personnel, and is inflated with a fluid such as a sterile solution. The pregnant woman may then perform the first movement 114, thus allowing her to relatively quickly achieve an approximate adjustment of the traction force applied on the balloon catheter 500 to reach a first level of traction force 120 that is roughly lower than a predefined comfort level 122, as typically recommended by medical personnel, and as illustrated graphically in FIG. 14. The pregnant woman may then perform the second movement 118 so as to reach a relatively higher and more precise second level of traction force 124 on the balloon catheter 500 such that the second level of traction force 124 is significantly closer to the predefined limit of comfort 122 recommended by the medical personnel and, thus, reaching the predefined comfort level with a relatively low risk of surpassing this level.

Still referring to FIG. 14, it can be observed that the first level of traction force 120 increases in a substantially proportional manner along with the progression of the first movement 114, while the second level of traction force 124 increases at a slightly lower rate relative to the progression of the second movement 118. Therefore, a more controlled or precise second level of traction force 124 may be achieved using the second movement 118 compared to the first movement 114. Thus, with the present invention, an advantage over conventional methods of maintaining a traction force on a balloon catheter resides in that the pregnant woman may substantially safely and easily self-readjust the level of traction force on the balloon catheter 500 each time she feels that the dilatation of her cervix has progressed. Hence, by using the present invention, significant amounts of time and operational costs by the medical personnel may be saved. A concurrent advantage of the present invention is that the pregnant woman may constantly monitor the level of traction force applied on the balloon catheter 500. This constant monitoring may significantly accelerate the overall progression of the dilatation, as opposed to substantially intermittent follow-ups by medical personnel using, for example, the conventional method with an adhesive tape. Further advantageously, the pregnant woman can self-apply a predefined sequence of varying traction force levels that can be repeated over time, to further promote the dilatation of her cervix. For example, the pregnant woman may apply and maintain a traction force for 10 to 15 seconds, then pause for another 10 to 15 seconds, and repeat the same sequence until the device falls out. Thus, proper maturation of the cervix may be achieved in a relatively shorter period of time compared to the conventional method using an adhesive tape. In cases of a pregnant woman previously having given birth, there have been maturation times of down to 2 minutes. The time for achieving maturity will also depend on parity (whether the woman has previously delivered or not), among other factors as maternal health professionals can appreciate.

Referring now to FIGS. 1 and 4, in a preferred embodiment of traction device 100, the stirrup element 102 is a closed loop element 126 suitably shaped and sized to freely and slideably engage through the aperture of an eyelet structure 128 connected to the catheter tube proximal end portion 504 (as best illustrated in FIG. 4). The closed loop element 126 is preferably made of a substantially flexible tubular member having a circular cross-section diameter of between 3 mm and 3 cm. Furthermore, the closed loop element 126 has an overall inner circumference that is suitably sized such that the stirrup distal end portion 106 sufficiently extends to engage around the foot forward end portion 512 when the underside or sole portion thereof is substantially located at the stirrup distal end first position 110, as illustrated in FIG. 10. In addition, at least a longitudinal portion of the stirrup element 102 is at least slightly resiliently stretchable for attenuating any abrupt traction force applied to the balloon catheter 500 by the foot forward end portion 512 of the pregnant woman. Thus, the risk of injuries and overall stress induced to the pregnant woman while using the traction device 100 may be significantly reduced. Advantageously, the tubular member may be represented by a commercially available tubular member typically included, for example, in IV tubing sets, or equivalent. Such tubular member inherently has a suitable diameter, as well as suitable flexibility and resilient stretching characteristics. In other embodiments, other equivalently flexible and resiliently stretchable elongated members may be used in the manufacture of the closed loop element 126. As it will be described further below, the stirrup element 102 is also preferably adjustable in length so as to suit the relative length of the leg of each pregnant woman using the traction device 100.

Referring now to FIGS. 10 and 11, the first movement 114 is at least a slightly forward pivotal movement of the foot forward end portion 512, and the second movement 118 is at least a slightly inward twisting movement of the foot forward end portion 512 about a longitudinal axis 130 thereof. Referring more particularly to FIG. 11, the slightly inward twisting movement of the foot forward end portion 512 during the second movement 118 is enabled by the closed loop element 126 sliding through the aperture of the eyelet structure 128. Thus, during the second movement 118, the two parallel segments of the closed loop element 126 on each side of the foot forward end portion 512 are each longitudinally moved in opposite directions, as indicated through reference 132.

Still referring to FIG. 11, as the second movement 118 progresses, an outer longitudinal edge of the foot forward end portion 512 stretches the stirrup element 102 at least slightly forwardly while, concurrently, the two parallel segments of the closed loop element 126 on each side of the foot forward end portion 512 get at least slightly closer to one another, which slightly counteracts the forward stretching effect of the foot outer edge 116. Due to this counter effect, the second level of traction force 124 raises at an at least slightly lower rate relative to the progression of the second movement 118, as illustrated in FIG. 14, hence the higher precision achieved. As is generally well known among persons familiar with various stretching exercise techniques of the lower limbs such as athletes, gymnastic coaches and yogis, a slightly less precise movement is generally achieved by a person performing a forward pivotal movement of the foot forward end portion 512 as per the first movement 114 than a slightly inward twisting movement of the foot forward end portion 512 as per the second movement 118.

Referring now to FIG. 2, there is shown an alternate embodiment of a traction device 200 according to the present invention. Traction device 200 is substantially similar to the traction device 100 described previously in that it includes a stirrup element 202 having a stirrup proximal end 204 connected to the catheter tube proximal end portion 504, and a stirrup distal end portion 206 configured for freely removably engaging the foot forward end portion 512 of the pregnant woman. In addition, the stirrup element 202 is preferably at least slightly resiliently stretchable in length, and also preferably adjustable in length. The preferred method of use of the traction device 200 is substantially similar to the previously described method of use illustrated in FIGS. 10 and 11, yielding similar resulting traction force profiles when applying the first and second movement 114 and 118 respectively, as illustrated in FIG. 14.

Still referring to FIG. 2, rather than the closed loop 126 configuration shown in FIG. 1, stirrup element 202 includes an elongated stirrup extension segment 240 connected at one end thereof to the catheter tube proximal end portion 504, and the other end terminated with a stirrup end loop segment 242. The stirrup end loop segment 242 is at least sufficiently sized for removably engaging the foot forward end portion 512. Furthermore, the stirrup end loop segment 242 defines a substantially smooth or non-adhering surface 244 along at least the whole inner circumference surface portion thereof contacting the underside, or sole surface of the foot forward end portion 512. Thus, the foot forward end portion 512 slips laterally relative to the smooth or non-adhering surface 244 of the stirrup end loop segment 242 as it progresses through the second movement 118. Hence, there is no opposite movement 132 of the stirrup segments on each side of the foot forward end portion 512 such as illustrated in FIG. 11. Hence, likewise the previously described embodiment of the traction device 100, the presently described traction device 200 enables the pregnant woman to apply a substantially controlled and thus precise second level of traction force 124 on the balloon catheter 500 through the second movement 118 compared to the first movement 114, as illustrated in FIG. 14. In an alternate embodiment, the stirrup extension segment 240 and stirrup end loop segment 242 may be formed out of a suitably extended catheter tube proximal end portion 504, whereby traction device 200 is an integral part of the balloon catheter 500.

Referring now to FIGS. 3, 12 and 13, there is shown an additional alternate embodiment of a traction device 300, according to the present invention. Traction device 300 is substantially similar to the traction devices 100, 200 described previously in that it includes a stirrup element 302 having a stirrup proximal end 304 connected to the catheter tube proximal end portion 504 and a stirrup distal end portion 306 configured for freely removably engaging the foot forward end portion 512 of the pregnant woman. Likewise, the stirrup element 302 is preferably at least slightly resiliently stretchable in length, and also preferably adjustable in length. Furthermore, the preferred method of use of the traction device 300 includes a similar first movement 114 of the foot forward end portion 512, as illustrated in FIG. 12.

Still referring to FIGS. 3, 12 and 13, the stirrup element 302 includes an elongated stirrup extension segment 340 connected at one end thereof to the catheter tube proximal end portion 504 and the other end terminated with a transversal toe engaging member 350, thus cooperatively forming a substantially T-shaped configuration therewith. The toe engaging member 350 and a proximally adjacent portion of the stirrup extension segment 340 are suitably shaped and sized to be comfortably engaged and retained between two toes of the foot 510, preferably the first two toes of the foot 510, as best illustrated in FIGS. 12 and 13. Furthermore, the second movement 118 is represented by a forward bending of the toes as illustrated in FIG. 13, rather than by twisting the foot forward end portion 512 such as illustrated in FIG. 11. Yet, as with previously-described traction devices 100, 200, the second movement 118 of the presently described embodiment of the traction device 300 enables the pregnant woman to apply a substantially controlled and thus more precise second traction force level 124 on the balloon catheter 500 through the second movement 118 compared to the first movement 114, as shown in FIG. 14. Referring more particularly to FIG. 13, as the forward bending of the toes progresses, the stirrup extension segment 340 is stretched along the extending roundness 514 of the surface of the foot 510 between the pair of toes through which is engaged the stirrup extension segment 340. As is generally well known among persons familiar with various stretching exercise techniques, a slightly less precise movement is generally achieved by a person performing the forward pivotal movement of the foot forward end portion 512 as per the first movement 114 than the forward bending movement of the toes as per the second movement 118.

Referring again to FIGS. 1 and 4, in some embodiments of the invention, the stirrup proximal end 104 is connected to the catheter tube proximal end portion 504 through a connector 160 having a tubular portion 162 fixedly and coaxially mounted to the catheter tube proximal end portion 504. Referring additionally to FIG. 5, in some embodiments the stirrup proximal end 104 is removably connected to the catheter tube proximal end portion 504 through a connector 164 defining a connector longitudinal slot 166. The connector longitudinal slot 166 has a suitably sized C-shaped cross-section for removably and transversally engaging in a snap-fit relation a longitudinal portion of the catheter tube proximal end portion 504. Referring additionally to FIG. 6, in some embodiments, the stirrup proximal end 104 removably connected to the catheter tube proximal end portion 504 through a connector 168 including a spring-biased manual clamp element 170 suitably shaped and sized for removably and transversally engaging a longitudinal portion of the catheter tube proximal end portion 504.

Referring now to FIG. 7, in some embodiments, the stirrup proximal end 204 is connected to the catheter tube proximal end portion 504 through a connector 160 having a tubular portion 162 fixedly and coaxially mounted to the catheter tube proximal end portion 504. Referring additionally to FIG. 8, in some embodiments, the stirrup proximal end 204 is removably connected to the catheter tube proximal end portion 504 through a connector 172 including a hook-and-loop fastener such as a Velcro® band 174 having one end portion fixedly connected to the connector 172 attached to the stirrup proximal end 204, and the remaining portion of the Velcro® band suitably shaped and sized for removably and transversally engaging a longitudinal portion of the catheter tube proximal end portion 504. Other types of connectors known by a person of skill in the art for connecting the stirrup proximal end of the stirrup element to the catheter tube proximal end portion 504 may also be used. Furthermore, as would be obvious to someone familiar with adjustable stirrups, the various removable means of connecting the stirrup proximal end to the catheter tube proximal end portion 504 such as connectors 164, 168 and 172 as described above, may also be used to selectively adjust the overall length of the stirrup element to suit the relative length of the leg of each pregnant woman using the traction device.

As exemplified in FIGS. 1, 2, 3 and 9, in some embodiments, the traction device 100, 200, 300 may further include an adjustment element 180 connected to the stirrup element 102, 202, 302 between the stirrup proximal end 104, 204, 304 and the stirrup distal end portion 106, 206, 306 thereof, for selectively adjusting the overall length of the stirrup element 102, 202, 302. Thus, with the traction device 100, 200, 300 connected to the balloon catheter 500, the overall length of the stirrup element 102, 202, 302 may be selectively adjusted so as to have the stirrup distal end portion 106, 206, 306 sufficiently extend to engage the foot 510 while being located at the stirrup distal end first position 110, as illustrated in FIGS. 10 and 12. Preferably, as best illustrated in FIG. 9, the adjustment element 180 includes a lever clamp 182 configured for adjusting in a sliding knot fashion a longitudinal portion of the stirrup element. The lever clamp 182 is a known type of clamp in the art wherein the adjustable longitudinal portion of the stirrup element 102, 202, 302 includes a separation, thus defining oppositely facing free ends, and wherein one free end is connected to the lever clamp 182 (represented in FIG. 9 by catheter tube proximal end portion 504). The other free end 305 is typically freely slideably engaged in a passageway extending through the lever clamp 182 and along which a pivotable lever 184 allows to selectively secure the free end thus engaged therein in a pinch-fashion. In other embodiments, other known equivalent types of adjustment element 180 are also possible.

Referring to FIG. 15, in some embodiments of the invention, the traction device 100, 200 further includes a removable stirrup holder 190 configured for maintaining a distal portion of the stirrup element 102 substantially in position across the underside, or sole, of the foot forward end portion 512. As exemplified in the figure, stirrup holder 190 includes a foot band 192 having a stirrup guide 194, such as a tubular passageway or equivalent, extending transversally across the sole of the foot forward end portion 512 and through which is freely slideably engaged a portion of the stirrup element 102. Preferably, the stirrup holder 180 is made of an at least slightly flexible and substantially soft surfaced material such as medical grade silicone, a polyester fabric, or the like. In other embodiments, other structures with similar functionality to the foot band 192 may be used, for example a foot cap or a sock or a cushion under the foot or sandals.

Referring to FIGS. 16 and 17, the traction device is shown being used by a pregnant woman with a single foot, according to an embodiment of the present invention. This version of the device uses one stirrup 102. The syringe 501 is used to fill the balloon that is shown in FIGS. 1 to 3. The movement of the entire leg associated with the stirrup is used to provide the appropriate traction force on the device. The stirrup 102 is fixed to the end of tube 505. As persons skilled in the art will understand, the device may be used with a single stirrup on a single foot.

Referring to FIGS. 18 and 19, the traction device is shown being used by a pregnant woman with her two feet, according to an embodiment of the present invention. This version of the device uses two stirrups 102, that is one stirrup on each foot. The syringe 501 is used to fill the balloon that is shown in FIGS. 1 to 3. The movement of the entire leg associated with each stirrup is used to provide the appropriate traction force on the device. Each stirrup 102 is fixedly connected to the end of tube 505. As persons skilled in the art will understand, the device may be used with a single stirrup on a single foot.

Although the present invention has been described hereinabove by way of preferred embodiments, the scope of the claims should not be limited by the preferred embodiments set forth in the examples, but should be given the broadest interpretation consistent with the description as a whole.

The invention claimed is:

1. A foot operated traction device for allowing a pregnant woman to selectively self-induce dilatation of her cervix via her foot, the device comprising:
   a balloon catheter comprising an inflatable balloon insertable above the cervix of the pregnant woman and an elongate catheter tube comprising a catheter tube proximal end portion and a catheter tube distal end portion coaxially mounted to said inflatable balloon, said inflatable balloon inflatable with a fluid to apply dilatative pressure against the cervix; and
   an elongate stirrup connected to said catheter tube at said catheter tube proximal end at a stirrup proximal end and removably engageable with the foot of the pregnant woman at a stirrup distal end;
   wherein said stirrup proximal end is axially fixed to said catheter tube proximal end portion via a connector;

wherein said stirrup distal end is movable by the movement of the foot to selectively vary a traction force of said inflatable balloon.

2. The device (100, 200, 300) of claim 1, wherein said stirrup distal end (106, 206, 306) is engageable with the foot (510) of the pregnant woman at a foot forward end portion (512).

3. The device (100, 200, 300) of claim 2, wherein said stirrup distal end (106, 206, 306) is movable between a stirrup distal end first position (110) and a stirrup distal end second position (112), said stirrup distal end second position (112) positioned further away from the cervix than said stirrup distal end first portion (110), through a first movement (114) of said foot forward end portion (512).

4. The device (100, 200, 300) of claim 3, wherein said stirrup distal end (106, 206, 306) is further movable between said stirrup distal end second position (112) and a stirrup distal end third position (116), said stirrup distal end third position (116) positioned further away from the cervix than said stirrup distal end second position (112), through a second movement (118) of said foot forward end portion (512).

5. The device (100, 200, 300) of claim 4, wherein said second movement (118) comprises at least one of an inward twisting movement of said foot forward end portion (512) about a longitudinal axis (130) thereof and a forward bending of the toes of the foot (510).

6. The device (100, 200, 300) of claim 4, wherein said second movement (118) increases said traction force at a lower rate than said first movement (114).

7. The device (100, 200, 300) of claim 3, wherein said first movement (114) comprises a forward pivotal movement of said foot forward end portion (512).

8. The device (300) of claim 2, wherein said elongate stirrup (302) comprises an elongated stirrup extension segment (340) connected at one end thereof to said catheter tube proximal end portion (504) and at another end thereof to a transversal toe engaging member (350) comprising a substantially T-shaped configuration and engageable and retainable between two toes of the foot (510).

9. The device (100, 200) of claim 2, further comprising a removable stirrup holder (190) comprising a foot band (192) comprising a stirrup guide (194), said removable stirrup holder (190) configured for maintaining a distal portion of sais stirrup element (102, 202) substantially in position across the underside of said foot forward end portion (512).

10. The device (100) of claim 1, wherein said elongate stirrup (102) comprises a closed loop element (126) slideably engagable with an eyelet structure (128) connecting said elongate stirrup (102) to said catheter tube proximal end portion (504).

11. The device of claim 10, wherein the connector is one of a connector comprising a tubular portion fixedly and coaxially mounted to said catheter tube proximal end portion, a connector comprising a connector longitudinal slot comprising a C-shaped cross section removably and transversally engageable with said catheter tube proximal end portion, or a connector comprising a spring-biased manual clamp element removably and transversally engageable with said catheter tube proximal end portion.

12. The device (200) of claim 1, wherein said elongate stirrup (202) comprises an elongated stirrup extension segment (240) connected at one end thereof to said catheter tube proximal end portion (504) and at another end thereof to a stirrup end loop segment (242).

13. The device of claim 12, wherein one of the connectors is a connector comprising a tubular portion fixedly and coaxially mounted to said catheter tube proximal end portion or a connector comprising a hook-and-loop fastener removably and transversally engageable with said catheter tube proximal end portion.

14. The device (100, 200, 300) of claim 1, further comprising an adjustable element (180) connected to said stirrup element (102, 202, 302) between said stirrup proximal end (104, 204, 304) and said stirrup distal end (106, 206, 306), said adjustable element (180) configured to adjust the length of sais stirrup element (102, 202, 302).

15. The device of claim 1, comprising a syringe (501) for filling the balloon (508) with fluid or air.

* * * * *